United States Patent
Chan et al.

(10) Patent No.: US 11,219,586 B2
(45) Date of Patent: Jan. 11, 2022

(54) COMPOSITIONS AND METHODS FOR DELIVERING CANNABINOIDS TO SKIN

(71) Applicant: Amyris, Inc., Emeryville, CA (US)

(72) Inventors: Diva Chan, Emeryville, CA (US); Ro Oteri, Emeryville, CA (US); Ashlee Nunes, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 0 days.

(21) Appl. No.: 17/375,512

(22) Filed: Jul. 14, 2021

(65) Prior Publication Data

US 2021/0338549 A1  Nov. 4, 2021

Related U.S. Application Data (60) Division of application No. 17/206,588, filed on Mar. 19, 2021, which is a continuation of application No. PCT/US2020/059357, filed on Nov. 6, 2020.

(60) Provisional application No. 62/931,978, filed on Nov. 7, 2019.

(51) Int. Cl.
| | |
|---|---|
| *A61K 31/01* | (2006.01) |
| *A61K 31/015* | (2006.01) |
| *A61K 31/045* | (2006.01) |
| *A61K 8/34* | (2006.01) |
| *A61K 8/31* | (2006.01) |
| *A61Q 19/00* | (2006.01) |

(52) U.S. Cl.
CPC ............... *A61K 8/347* (2013.01); *A61K 8/31* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 9,592,257 | B2 | 3/2017 | Wu et al. |
| 10,039,791 | B2 | 8/2018 | Bakkar et al. |
| 10,073,085 | B2 | 9/2018 | Akashi et al. |
| 10,150,265 | B1 | 12/2018 | Hart et al. |
| 10,323,230 | B2 | 6/2019 | Jeon et al. |
| 2016/0235661 | A1 | 8/2016 | Changoer |

(Continued)

FOREIGN PATENT DOCUMENTS

| | | |
|---|---|---|
| WO | 2016/133824 A1 | 8/2016 |
| WO | 2019/056129 A2 | 8/2019 |

OTHER PUBLICATIONS

Neossance, H&PC Today, 2015, 10(1) pp. 12-13. (Year 2015).

(Continued)

*Primary Examiner* — Brian Gulledge
(74) *Attorney, Agent, or Firm* — RinLaures LLC; Li-Hsien Rin-Laures; Kristen A. Dola (57) ABSTRACT

Provided herein are compositions for delivering one or more cannabinoids to the skin of a subject and methods of using the compositions to deliver the one or more cannabinoids to the skin of a subject. The compositions contain a carrier that facilitates the delivery and permeation of cannabinoids to and through the skin. The carriers of the compositions contain squalane or mixtures of squalane and hemisqualane. The compositions described herein may serve as the base for the preparation of various cosmetics or various pharmaceuticals. The cosmetics or pharmaceuticals may be used to reduce inflammation, control pain, or prevent aging of the skin of a subject.

20 Claims, 2 Drawing Sheets

(56) References Cited

U.S. PATENT DOCUMENTS

2019/0046438 A1* 2/2019 Hnat .................... A61K 31/522
2019/0247299 A1 8/2019 Cameron et al.

OTHER PUBLICATIONS

Amyris Unviels Hemisequalane Emollient and Second Personal Care Launch. Anderson, dated Nov. 18, 2014.
Lane, Skin penetration enhancers. Interntl. J. Pharmaceut. 447:12-21 (2013).

* cited by examiner

COMPOSITIONS AND METHODS FOR DELIVERING CANNABINOIDS TO SKIN

CROSS-REFERENCE TO RELATED APPLICATIONS

The present application is a Divisional Application of application Ser. No. 17/206,588, filed Mar. 19, 2021; which is a continuation of application Serial No. PCT/US20/59357, filed Nov. 6, 2020; which claims the benefit of application Ser. No. 62/931,978, filed Nov. 7, 2019, the entire disclosures of which are incorporated herein by reference.

FIELD OF THE INVENTION

The present disclosure relates to compositions comprising cannabinoids and carriers and methods of using the compositions to deliver the cannabinoids to the skin of a subject.

BACKGROUND

Cannabinoids are a group of structurally related molecules defined by their ability to interact with a distinct class of receptors (cannabinoid receptors). Both naturally occurring and synthetic cannabinoids are known. Naturally occurring cannabinoids are produced primarily by the *Cannabis* family of plants. An expanding set of synthetic variants of cannabinoids have been designed to mimic the effects of the naturally occurring molecules.

The various cannabinoids interact differentially with select cannabinoid receptors to produce distinct physiological responses. For example, tetrahydrocannabinol (THC) binding to the cannabinoid receptor 1 ($CB_1$) in the brain results in the psychoactive properties associated with marijuana use. In contrast, other cannabinoids preferentially react with the cannabinoid receptor 2 ($CB_2$) and lack the psychoactive effect of THC. Other cannabinoids, for example cannabidiol (CBD), have little affinity for either $CB_1$ or $CB_2$, but instead bind additional receptors (the GPR55 receptor in the case of CBD). This differential receptor binding has been proposed as the underlying basis for multiple potential pharmacological uses for cannabinoids, including: reducing nausea and vomiting, controlling pain, relieving anxiety, treating epilepsy, reducing inflammation, preventing the aging of the skin, and relaxing muscle tension.

The recent decriminalization of *Cannabis* by various states and countries has led to increased interest in the possible uses of cannabinoids. The plethora of potential uses of cannabinoids have led to a need for a diverse array of methods of delivering cannabinoids to various target tissues and cells. For example, exploitation of the anti-inflammatory, pain management, and anti-aging properties of cannabinoids requires robust methods of delivering cannabinoids to the skin. The present invention addresses the pressing need for compositions and methods of efficiently delivering cannabinoids to the skin of a subject.

SUMMARY OF THE INVENTION

Provided herein are compositions for the delivery and permeation of cannabinoids to and through skin and methods of delivering cannabinoids to the skin of a subject.

In one aspect, the invention provides for a composition containing a carrier and one or more cannabinoids, wherein the carrier contains squalane.

In an embodiment, the carrier also contains hemisqualane. In another embodiment, the squalane and hemisqualane are present in a ratio from about 10 to 1 (squalane to hemisqualane) by weight to about 1 to 10 (squalane to hemisqualane) by weight. In a further embodiment, the squalane and hemisqualane are present in a ratio of about 1 to 1 by weight. In yet another embodiment, the one or more cannabinoids comprises from about 0.01% w/w to about 10% w/w of the composition. In a preferred embodiment, the one or more cannabinoids comprises from about 0.3% w/w to about 1% w/w of the composition. In yet another embodiment, the one or more cannabinoids comprises about 0.7% w/w of the composition.

In an embodiment of the invention, the squalane is from about 10% w/w to about 99.9% w/w of the composition. In another embodiment, the one or more cannabinoids is selected from cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), tetrahydrocannabinol (THC), and tetrahydrocannabinolic acid (THCA). In a preferred embodiment, the composition contains cannabidiol (CBD).

In another aspect, the invention provides for a cosmetic containing a carrier and a cannabinoid, wherein the carrier comprises squalane. In an embodiment, the cosmetic also contains one or more excipients selected from natural oils, synthetic oils, emulsifiers, emollients, lipids, humectants, moisturizers, binders, conditioning agents, emulsion stabilizing salts, preservatives, chelating agents, sequestering agents, abrasives, pH adjusters, surfactants, perfumes, and colorings. In an embodiment, the carrier in the cosmetic contains both squalane and hemisqualane. In yet another embodiment, the squalane and hemisqualane are present in a ratio of about 10 to 1 (squalane to hemisqualane) by weight to about 1 to 10 (squalane to hemisqualane) by weight. In a further embodiment, the cannabinoid is selected from cannabidiol (CBD), cannabidiolic acid (CBDA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabielsoin (CBE), cannabicitran (CBT), tetrahydrocannabinol (THC), tetrahydrocannabinolic acid (THCA), and combinations thereof. In a preferred embodiment, the cosmetic contains cannabidiol (CBD).

In a further aspect, the invention provides a method of delivering a cannabinoid to a subject involving applying the composition of the invention to a skin area of the subject. In an embodiment, the composition is applied to the skin area in an amount of from about 0.1 mg/cm$^2$ to about 10 mg/cm$^2$. In another embodiment, the composition is applied to the skin area in an amount of from about 1 mg/cm$^2$ to about 3 mg/cm$^2$. In a further embodiment, an effective amount of cannabinoid is delivered to the subject.

In an additional aspect, the invention provides a method of reducing inflammation in skin of a subject involving administering an effective amount of the composition of any one of the invention to the skin of the subject, thereby reducing inflammation. In an embodiment, the composition is administered to the skin area in an amount of from about 0.1 mg/cm$^2$ to about 10 mg/cm$^2$. In yet another embodiment, the composition is administered to the skin area in an amount of from about 1 mg/cm$^2$ to about 3 mg/cm$^2$. In an additional embodiment, the composition is administered at least daily. In further embodiments, the composition is adminstered at least twice daily.

DETAILED DESCRIPTION OF THE EMBODIMENTS

The invention provides compositions useful for delivering cannabinoids to the skin of a subject, wherein the carrier used to deliver the cannabinoids is squalane or a mixture of squalane and hemisqualane. The invention also provides methods of delivering a cannabinoid to the skin of the subject involving the administration or application of a composition containing the cannabinoid and a carrier where the carrier may be squalane or a mixture of squalane and hemisqualane.

As used herein an "effective amount" means an amount necessary to at least partly attain the desired response, or to delay the onset or inhibit progression or halt altogether, the onset or progression of a particular symptom being treated. The amount varies depending upon the health and physical condition of the subject to be treated, the taxonomic group of subject to be treated, the degree of protection desired, the formulation of the composition, the assessment of the medical situation, and other relevant factors. It is expected that the amount will fall in a relatively broad range that can be determined through routine trials.

As used herein, "subject" or "patient" is an organism that is treated using one of the methods of the present disclosure. In an embodiment, the subject is a mammalian subject, such as a human or a domestic animal.

As used herein, the term "about" will be understood by persons of ordinary skill in the art and will vary to some extent on the context in which is used. If there are uses of the term which are not clear to persons of ordinary skill in the art given the context in which is used, "about" may mean up to plus or minus 20% of the particular term.

As used herein, the term "ointment" may be any commonly known and commercially available ointments.

As used herein a "cannabinoid" is a species of a genus of molecules referred to as "cannabinoids" that bind to cannabinoid receptors. Cannabinoids may be isolated from the *Cannabis* family of plants including *Cannabis sativa, Cannabis indica*, and *Cannabis ruderalis. Cannabis sativa* L., also referred to as "hemp," is a subspecies of *Cannabis* used for the production of cannabinoids because of its inability to produce significant levels of the psychoactive cannabinoids (THCA and THC). Cannabinoids may also be made using synthetic biology, where microorganisms are created that express the gene products necessary to produce one or more cannabinoids. In addition, cannabinoids may be made synthetically from organic precursor molecules using standard organic chemical methods.

As used herein "cannabidiol" or "CBD" is a cannabinoid having the following structure:

As used herein "cannabidiolic acid" or "CBDA" is a cannabinoid having the following structure:

As used herein "cannabinol" or "CBN" is a cannabinoid having the following structure:

As used herein "cannabigerol" or "CBG" is a cannabinoid having the following structure:

As used herein "cannabichromene" or "CBC" is a cannabinoid having the following structure:

As used herein "cannabicyclol" or "CBL" is a cannabinoid having the following structure:

As used herein "cannabivarin" or "CBV" is a cannabinoid having the following structure:

As used herein "tetrahydrocannabivarin" or "THCV" is a cannabinoid having the following structure:

As used herein "cannabidivarin" or "CBDV" is a cannabinoid having the following structure:

As used herein "cannabichromevarin" or "CBCV" is a cannabinoid having the following structure:

As used herein "cannabigerovarin" or "CBGV" is a cannabinoid having the following structure:

As used herein "cannabigerol monomethyl ether" or "CBGM" is a cannabinoid having the following structure:

As used herein "cannabielsoin" or "CBE" is a cannabinoid having the following structure:

As used herein "cannabicitran" or "CBT" is a cannabinoid having the following structure:

As used herein "tetrahydrocannabinol" or "THC" is a cannabinoid having the following structure:

As used herein "tetrahydrocannabinolic acid" or "THCA" is a cannabinoid having the following structure:

As used herein, "carrier" refers to a compound that facilitates the delivery of a cannabinoid to the skin of a subject. Preferred carriers include squalane and mixtures of squalane and hemisqualane. Other carriers include derivatives of squalane including squalene, neosqualane, and isosqualene.

As used herein, "squalane" refers to a compound having the following formula:

As used herein "hemisqualane" or "farnesane" refers to a compound having the following structure:

or a stereoisomer thereof.

As used herein, "iso-squalane" or "isosqualane" refers to a compound having the following formula:

As used herein, "neosqualane" refers to a compound having the following formula:

As used herein, "squalene" refers to a compound having the following formula:

As used herein, "iso-squalene" or "isosqualene" refers to a compound having any one of the following structures:

;

Compositions and cosmetics disclosed herein may comprise various amount per weight of carrier comprising squalane. Examples include 10% (w/w), 15% (w/w), 20% (w/w), 25% (w/w), 30% (w/w), 35% (w/w), 40% (w/w), 45% (w/w), 50% (w/w), 55% (w/w), 60% (w/w), 65% (w/w), 70% (w/w), 75% (w/w), 80% (w/w), 85% (w/w), 86% (w/w), 87% (w/w), 88% (w/w), 89% (w/w), 90% (w/w), 91% (w/w), 92% (w/w), 93% (w/w), 94% (w/w), 95% (w/w), 96% (w/w), 97% (w/w), 98% (w/w), 99% (w/w), 99.1% (w/w), 99.2% (w/w), 99.3% (w/w), 99.4% (w/w), 99.5% (w/w), 99.6% (w/w), 99.7% (w/w), 99.8% (w/w), and 99.9% (w/w) carrier comprising squalane. Preferred embodiments comprise at least 90% (w/w) of carrier comprising squalane.

Carriers comprising mixtures of squalane and another carrier may be used in the compositions and cosmetics. A preferred carrier mixture comprises squalane and hemisqualane. Squalane and hemisqualane may be mixed in various ratios based on weight. Illustrative example ratios of squalane to hemisqualane include 10 to 1, 5 to 1, 10 to 3, 5 to 2, 2 to 1, 5 to 3, 10 to 7, 5 to 4, 10 to 9, 1 to 1, 9 to 10, 4 to 5, 7 to 10, 3 to 5, 1 to 2, 2 to 5, 3 to 10, 1 to 5, and 1 to 10. A person of skill in the art would understand that intermediate ratios between these values could also be derived to form a carrier comprising squalane and hemisqualane. A preferred embodiment involves a mixture of squalane and hemisqualane mixed at a 1 to 1 ratio by weight.

Compositions comprising a carrier comprising squalane may contain an amount of cannabinoid dictated by the use of the composition. Cannabinoids may be present in the compositions at a certain weight percentage (w/w). For example, cannabinoids may comprise 0.01% (w/w), 0.02% (w/w), 0.03% (w/w), 0.04% (w/w), 0.05% (w/w), 0.06% (w/w), 0.07% (w/w), 0.08% (w/w), 0.09% (w/w), 0.10% (w/w), 0.11% (w/w), 0.12% (w/w), 0.13% (w/w), 0.14% (w/w), 0.15% (w/w), 0.16% (w/w), 0.17% (w/w), 0.18% (w/w), 0.19% (w/w), 0.20% (w/w), 0.25% (w/w), 0.30% (w/w), 0.35% (w/w), 0.40% (w/w), 0.45% (w/w), 0.50% (w/w), 0.55% (w/w), 0.60% (w/w), 0.65% (w/w), 0.70% (w/w), 0.75% (w/w), 0.80% (w/w), 0.85% (w/w), 0.90% (w/w), 0.95% (w/w), 1.0% (w/w), 1.1% (w/w), 1.2% (w/w), 1.3% (w/w), 1.4% (w/w), 1.5% (w/w), 1.6% (w/w), 1.7% (w/w), 1.8% (w/w), 1.9% (w/w), 2.0% (w/w), 2.1% (w/w), 2.2% (w/w), 2.3% (w/w), 2.4% (w/w), 2.5% (w/w), 2.6% (w/w), 2.7% (w/w), 2.8% (w/w), 2.9% (w/w), 3.0% (w/w), 3.5% (w/w), 4.0% (w/w), 4.5% (w/w), 5.0% (w/w), 5.5% (w/w), 6.0% (w/w), 6.5% (w/w), 7.0% (w/w), 7.5% (w/w), 8.0% (w/w), 8.5% (w/w), 9.0% (w/w), 9.5% (w/w), and 10% (w/w). In some embodiments, the maximum amount of cannabinoid comprising the composition will be limited by the solubility limit of the cannabinoid in the carrier. In those cases, the maximum amount of cannabinoid can be determined empirically.

As used herein, the term "cosmetic" or "cosmetic composition" means any substance or mixture intended to be placed in contact with various external parts of a subject's body (epidermis, hair systems, nails, lips, and external sex organs) or with the teeth and the mucous membranes of the oral cavity with the intent primarily to clean, perfume, or changing the appearance of the subject's body, teeth, or mucous membranes of the oral cavity.

Cosmetics of the invention may contain one or more excipients. Excipients include but are not limited to natural oils, synthetic oils, emulsifiers, emollients, lipids, humectants, moisturizers, binders, conditioning agents, emulsion stabilizing salts, preservatives, chelating agents, sequestering agents, abrasives, pH adjusters, surfactants, perfumes and colorings.

The invention provides for the use of squalane and squalane/hemisqualane as a carrier in the cosmetic to facilitate the delivery of cannabinoids when applied topically to the skin.

However, one skilled in the art will readily appreciate, embodiments of the cosmetic of the invention may include other carriers or vehicles (hereinafter "cosmetic base(s)") in addition to squalane or squalane/hemisqualane. Generally, the cosmetic base may be grouped in four classes: oleaginous bases; emulsifiable bases; emulsion bases; and water-soluble bases. See, e.g., Remington: The Science and Practice of Pharmacy, 19th Ed. (Easton, Pa.: Mack Publishing Co., pp. 1301-1306 (1985). Oleaginous ointment bases include, for example, vegetable oils, synthetic oleaginous esters of carboxylic acids and alcohols, fats obtained from animals, semisolid hydrocarbons obtained from petroleum and the like.

Examples of oleaginous cosmetic bases include white ointment, yellow ointment, cetyl esters wax, paraffins, petrolatum, white petrolatum, white wax, yellow wax, beeswax, and the like and mixtures thereof. Emulsifiable cosmetic bases, also known as absorbent ointment bases, contain little or no water and include, for example, hydroxystearic sulfate, anhydrous lanolin, hydrophilic petrolatum and the like and mixtures thereof. Emulsion cosmetic bases are either water-in-oil (W/O) emulsions, or oil-in-water (O/W) emulsions, and can include, for example, cetyl alcohol, lanolin, glyceryl monostearate, stearic acid and the like and mixtures thereof. Useful water-soluble ointment bases can be those prepared from glycol ethers such as, for example, polyethylene glycols of varying molecular weight, polysorbates and the like and mixtures thereof. Petrolatum may be at a concentration of greater than or equal to 50%, preferably greater than or equal to 70%, for example.

In some embodiments of this aspect, the C11-C40 alcohol or the C11-C40 carboxylic acid, or combinations thereof may be present in an amount of about 0.1% to about 20%, preferably 0.1 to 15%, more preferably 0.1 to 10%, for example, of the composition by weight. In certain embodiments, the C11-C40 alcohol may be a terminally functionalized alkyl alcohol having 11 to 40 carbon atoms, preferably having 16 to 40 carbon atoms, more preferably 20 to 40 carbon atoms, for example.

The general formula of the terminally functionalized alkyl alcohols are: Rn(OH), wherein n is equal to or greater than 11 and equal to or less than 40; wherein R is a saturated or unsaturated hydrocarbon chain. Examples of saturated and unsaturated alkyl alcohols suitable for preparing the compositions of the present embodiment are 1-dodecanol, 1-tridecanol, 1-tetradecanol, 1-pentadecanol, 1-hexadecanol, 1-heptadecanol, 1-octadecanol, 1-nonadecanol, 1-eicosanol, 1-heneicosanol, 1-docosanol, 1-tetracosanol, 1-hexacosanol, 1-heptacosanol, 1-octacosanol, 1-nonacosanol, 1-triacontanol, 1-dotriacontanol, 1-tetratriacontanol, tridecyl alcohol, palmitoleyl alcohol, erucyl alcohol, and combinations thereof. Lanolin alcohol is also suitable.

In certain embodiments, the C11-C40 acids may be terminally functionalized alkyl carboxylic acids having a general formula: Rn(COOH), wherein n is equal to or greater than 11 and equal to or less than 40. In one embodiment, R may be a saturated or unsaturated hydrocarbon chain.

Examples of saturated carboxylic acids suitable for preparing the extracts and compositions of the present embodiment are lauric acid, tridecylic acid, myristic acid, pentadecyclic acid, palmitic acid, margaric acid, stearic acid, nonadecyclic acid, arachidic acid, heneicosylic acid, benenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, octatriacontanoic acid, and combinations thereof.

Examples of unsaturated carboxylic acids suitable for preparing the compositions of the present embodiment are myristoleic acid, palmitoleic acid, α-linolenic acid, linoleic acid, stearidonic acid, γ-linolenic acid, vaccenic acid, oleic acid, elaidic acid, sapienic acid, eicosapentaenoic acid, dihomo-γ-linolenic acid, arachidonic acid, paullinic acid, gondoic acid, erucic acid, docosahexaenoic acid, docosatetraenoic acid, linoelaidic acid, eicosapentaenoic acid, nervonic acid, sardine acid, herring acid, mead acid, and combinations thereof.

Salts of the unsaturated and saturated carboxylic acids are also suitable for preparing the compositions of the present embodiment. Examples include sodium stearate, magnesium stearate, sodium behenate, sodium oleate, calcium oleate, magnesium oleate, sodium linoleate, and combinations thereof.

The polymer in the compositions may be at a concentration of about 0.1% to about 20%, preferably about 0.1 to about 15%, more preferably about 0.1 to about 10%.

The polymer might be poly α-olefins, polyaromatics, or fluoropolymers. Examples of poly α-olefins include polyethylene, polypropylene, polybutylene, poly-1-hexadecene, and poly-1-eicosene. Examples of polyaromatics include polystyrene, substituted polystyrene. Examples of fluoropolymers include polyvinylidene fluoride, polyvinyl fluoride.

The polymer might also be a copolymer. Examples of monomers in the copolymer include vinyl monomers, styrene and functionalized styrene monomers, and α-olefins. In one embodiment, the olefin may comprise α-olefins having at least 11 carbon atoms. It is believed that a copolymer comprising different monomer units is generally preferred for its ability to loosen and disrupt dense and orderly packing of hydrocarbons in petrolatum than a polymer comprising only same monomer units. Furthermore, a copolymer with different monomer units might help dispersion and solubilization of the active agents. Therefore, a copolymer is preferred.

Examples of vinyl monomers include vinyl acetate, maleic acid, and vinyl pyrrolidone. A copolymer of vinyl monomers and α-olefins is preferred. According to the present embodiment, the copolymer needs to be solubilized in the composition base comprising petrolatum. Hydrophobicity of α-olefins increases as the chain length increases. Due to highly hydrophobic nature of the petrolatum base, long chain α-olefins are believed to make the copolymer more soluble in the composition comprising petrolatum. Therefore, copolymers of vinyl monomers and long chain α-olefins are preferred. The long chain α-olefins may have at least 11 carbon atoms, preferably at least 16 carbon atoms, more preferably at least 20 carbon atoms.

Because of the occlusive, emollient, and non-irritating properties of petrolatum, it is desirable to maintain these desirable properties. Therefore, the release enhancing agents, such as alcohols, acids or polymers may be present in an amount of about 0.1 to about 20%, preferably about 0.1 to about 15%, more preferably about 0.1 to about 10%, more preferably about 0.1% to about 5%.

Examples of the cosmetically active agents include vitamins, such as vitamin B, vitamin C, tocopherols (vitamin E), tocopherol derivatives, tocotrienols, vitamin D, K and derivatives thereof, and suitable combinations thereof, for example.

Moisturizing compounds may include glycerin, urea, methylurea, ethylurea, allantoin, lactates, sugars, methyl glucose ethers, sodium pyrrolidone carboxylic acid, sodium hyaluronate, panthenol, hyaluronic acid, α- and β-hydroxyl acids, such as glycolic acid, lactic acid, mandelic acid, or salicylic acid, or combinations of the suitable moisturizing compounds, for example.

The compositions containing the extracts may further comprise a penetration enhancer, such as tissue penetration enhancers, to enhance release and delivery of the active compound into tissues, such as, for example, skin, ocular, nasal. For these compositions, they might comprise both release enhancing agents of the present embodiment and tissue penetration enhancers. The tissue penetration enhancers may then enhance tissue absorption and penetration of the released active agent. The tissue penetration enhancers might be either in suspended solid or solubilized form in the compositions of the present embodiment.

Tissue penetration enhancers, such as suitable volatile organic solvents, include aliphatic, cycloaliphatic and/or aromatic-aliphatic alcohols, each of which is monohydric or polyhydric, alcohol/water mixtures, saturated and/or unsaturated fatty alcohols which each contains from about 8 to about 18 carbon atoms, saturated and/or unsaturated fatty acids which each contains from about 8 to about 18 carbon atoms and/or esters thereof and the like and mixtures thereof. Useful alcohols are those having from 1 to about 20 carbon atoms, e.g., ethanol, isopropyl alcohol, 1-butanol, 1-octanol, etc.

The compositions of the invention can be administered or applied in a variety of unit dosage forms depending upon the method of administration or application. Dosages for typical cannabinoid compounds are well known to those of skill in the art. Such dosages are typically advisory in nature and are adjusted depending on the particular therapeutic context, patient or organ tolerance, etc. The amount of cannabinoid contained in the composition adequate to accomplish this is defined as an "effective dose." The dosage schedule and amounts effective for this use, i.e., the "administration regimen," will depend upon a variety of factors. In calculating the administration regimen for skin, the mode of administration or application also is taken into consideration. The administration or application regimen must also take into consideration the pharmacokinetics, i.e., the cannabinoid's or composition's rate of absorption, bioavailability, metabolism, clearance, and the like. (See, e.g., the latest Remington's; Egleton and Davis 1997 Peptides 18:1431-1439; Langer 1990 Science 249:1527-1533).

The compositions and cosmetics provided herein may be applied to any available skin area that is in need of treatment. In some embodiments the composition or cosmetic is applied to the skin area liberally such that the skin area is saturated with the composition or cosmetic. In other embodiments it would be preferable to apply a specific amount of the composition or cosmetic to a specific amount of skin area (for example 1 mg composition per 1 $cm^2$ skin area). The compositions and cosmetics may be applied at 0.1 $mg/cm^2$, 0.2 $mg/cm^2$, 0.3 $mg/cm^2$, 0.1 $mg/cm^2$, 0.4 $mg/cm^2$, 0.5 $mg/cm^2$, 0.6 $mg/cm^2$, 0.7 $mg/cm^2$, 0.8 $mg/cm^2$, 0.9 $mg/cm^2$, 1.0 $mg/cm^2$, 1.1 $mg/cm^2$, 1.2 $mg/cm^2$, 1.3 $mg/cm^2$, 1.4 $mg/cm^2$, 1.5 $mg/cm^2$, 1.6 $mg/cm^2$, 1.7 $mg/cm^2$, 1.8 $mg/cm^2$, 1.9 $mg/cm^2$, 2.0 $mg/cm^2$, 2.1 $mg/cm^2$, 2.2 $mg/cm^2$, 2.3 $mg/cm^2$, 2.4 $mg/cm^2$, 2.5 $mg/cm^2$, 2.6 $mg/cm^2$, 2.7 $mg/cm^2$, 2.8 $mg/cm^2$, 2.9 $mg/cm^2$, 3.0 $mg/cm^2$, 3.5 $mg/cm^2$, 4.0 $mg/cm^2$, 4.5 $mg/cm^2$, 5.0 $mg/cm^2$, 5.5 $mg/cm^2$, 6.0 $mg/cm^2$, 6.5 $mg/cm^2$, 7.0 $mg/cm^2$, 7.5 $mg/cm^2$, 8.0 $mg/cm^2$, 8.5 $mg/cm^2$, 9.0 $mg/cm^2$, 9.5 $mg/cm^2$, and 10.0 $mg/cm^2$. In preferred embodiments the composition or cosmetic is applied at from about 1 $mg/cm^2$ to about 3 $mg/cm^2$.

The compositions and cosmetics may be applied as needed to ameliorate the condition or symptom being treated. In embodiments the compositions and cosmetics are applied at least once daily. In preferred embodiments the compositions and cosmetics are applied at least twice daily.

The compositions provided herein may be tested or optimized through use of skin models. Appropriate skin models are well known in the art and have been described in U.S. Pat. Nos. 10,323,230; 10,150,265; 10,073,085; and 9,592,257, each of which is incorporated in their entirety herein. A preferred skin model is commercially available as EPISKIN, and has been described at least in U.S. Pat. No. 10,039,791. In a typical skin model, cultured cells representing the predominant cell types of the epidermis are cultured as flat sheets on a support. In a preferred method, a three-dimensional culture of the cells is grown on the membrane of a cell well insert. Such a configuration allows for the positioning of the external (outer layer) of the reconstructed skin to be exposed to the upper surface of the insert and the basal cell layer of the reconstructed skin to be exposed to the lower or membrane surface of the insert. After reconstitution, the cells are cultured under defined conditions in cell culture media whereupon the cells fully differentiate and form the reconstructed skin layer. The use of cell wells and cell well inserts allows for experiments testing the delivery or permeation of skin by various test samples. In this configuration, the upper chamber of the insert is referred to as the "donor well" which contains the donor fluid. The chamber of the well in which the insert sits is the "receptor well" which contains the receptor fluid. In a typical delivery and/or permeation experiment, a test sample is applied to the donor well—in other words the test sample is applied to the surface of the reconstructed skin which represents the outer layer of the skin. The insert is then cultured at physiological temperature (37° C.) in a tissue culture incubator to maintain proper temperature, $CO_2$, and pH. At appropriate intervals, the donor fluid containing the test sample is removed, the cell insert is washed, and the samples are collected. Typically, three samples can be collected: the donor fluid, the skin cell fraction, and the receptor fluid. Each fraction can be assayed using the appropriate assay needed to measure the amount of the test compound in each fraction. In the case of cannabinoids, the amount of cannabinoid in each fraction can be determined by use of high-pressure liquid chromatography (HPLC). In HPLC, sample is loaded on an appropriate column and run with an appropriate mobile phase. Purified preparations of the cannabinoid are run as a standard. In this case, the compound can be identified by its retention time on the column and its concentration or amount can be determined by quantitating the area under the peak and deriving the amount using an algorithm determined by running known amounts of the control standard cannabinoid sample. The amount of compound in the skin cell fraction is an indication of the ability of the compound to be delivered into the skin cells. The amount of compound in the receptor fluid is an indication of the amount of compound able to permeate the entire skin layer.

EXAMPLES

Example 1: Squalane and Squalane/Hemisqualane Mixtures Facilitate Skin Penetration of Cannabinoid The ability of various carrier molecules to facilitate skin penetration and permeation of cannabinoid was evaluated using an in vitro model of human skin. A commercially available in vitro model of human skin (EPISKIN) was used according to the manufacture's instructions. The in vitro model is described in detail in U.S. Pat. No. 10,039,791, which is incorporated herein in its entirety. However, any number of well know in vitro skin models may be used. For example, skin models have been described in U.S. Pat. Nos. 10,323,230; 10,150,265; 10,073,085; and 9,592,257.

The EPISKIN model is a model involving reconstructed human epidermis (RhE) cultured in tissue culture inserts typically in a twelve (12) well plate. The fluid within the top of the insert is the donor fluid and the fluid below the insert is the receptor fluid.

Test samples were prepared by mixing cannabidiol (CBD) in one of three carriers: squalane, jojoba oil, and a 1:1 mixture of squalane and hemisqualane. For each carrier, CBD was added to a concentration of approximately 1% (w/w), see Table 1.

TABLE 1

CBD concentration (w/w) in test sample

| Sample | CBD concentration (w/w) | | | | | |
|---|---|---|---|---|---|---|
| | 1 | 2 | 3 | Mean | ± | SD |
| Squalane | 1.03 | 1.04 | 1.05 | 1.04 | ± | 0.01 |
| Jojoba oil | 1.04 | 1.03 | 1.05 | 1.04 | ± | 0.01 |
| Hemisqualane/Squalane mixture (1:1) | 1.02 | 1.02 | 1.01 | 1.02 | ± | 0.01 |

Each test sample was added to the donor fluid side of the in vitro skin tissue grown in culture. The details of the sample addition are shown in Table 2. The three-dimensional cultured skin model (EpiSkin-LM) were plated in the wells of twelve (12) well plates and conditioned overnight in maintenance medium. The maintenance medium was replaced with two (2) mL of 1% Tween in PBS solution for each well, and point one five (0.15) mL of the test sample was applied to the stratum corneum of the skin model and incubated at 37° C. for 1, 3, 6, or 24 hours. At each time point, the test sample was removed from the surface of the skin model and washed five times with 0.5 mL of the respective carrier used (squalane, jojoba oil, or 1:1 squalane/hemisqualane mixture depending on the test sample).

TABLE 2

CBD amount applied to skin model

| Sample | Applied sample amount (ml) | Specific gravity (g/ml) | CBD concentration (wt %) | Applied CBD amount (mg) |
|---|---|---|---|---|
| Squalane | 0.150 | 0.81 | 1.04 | 1.26 |
| Jojoba oil | 0.150 | 0.86 | 1.04 | 1.35 |
| Hemisqualane/Squalane mixture (1:1) | 0.150 | 0.79 | 1.02 | 1.21 |

For each test sample, three distinct types of samples were collected (skin cells, receptor fluid, and washing fluid) in triplicate at various time points (1, 3, 6, and 24 hours) and the amount of CBD in each sample was measured. For the skin cell samples, the washed cells were transferred to an Eppendorf tube and 1 mL of ethanol and a stainless-steel bead was added. The skin cells were then ground with a TissueLyser. The wash fluid was transferred to a 50 mL volumetric flask and diluted with isopropanol up to a volume of 50 mL. The amount of CBD in each sample (cell, receptor fluid, and wash) was determined by HPLC run under the following conditions:
 1. Detector: a photodiode array detector (208 nm).
 2. Column: a stainless-steel column 4.6 mm inside diameter and 100 mm long, packed with octadecylsilanized silica gel (2.7 μm particle diameter).
 3. Mobile phase: 0.1% formic acid acetonitrile (containing 0.1% formic acid)=3.7 (volume).
 4. Flow rate: 1.5 mL/minute.
 5. Column temperature: 50° C.
 6. Sample injection: 10 μL.

Calibration curve. Concentration (ppm)=2.3339× $10^{-5}$×peak area $R^2$=0.999(0.26~155.85 ppm).

Figure 1:
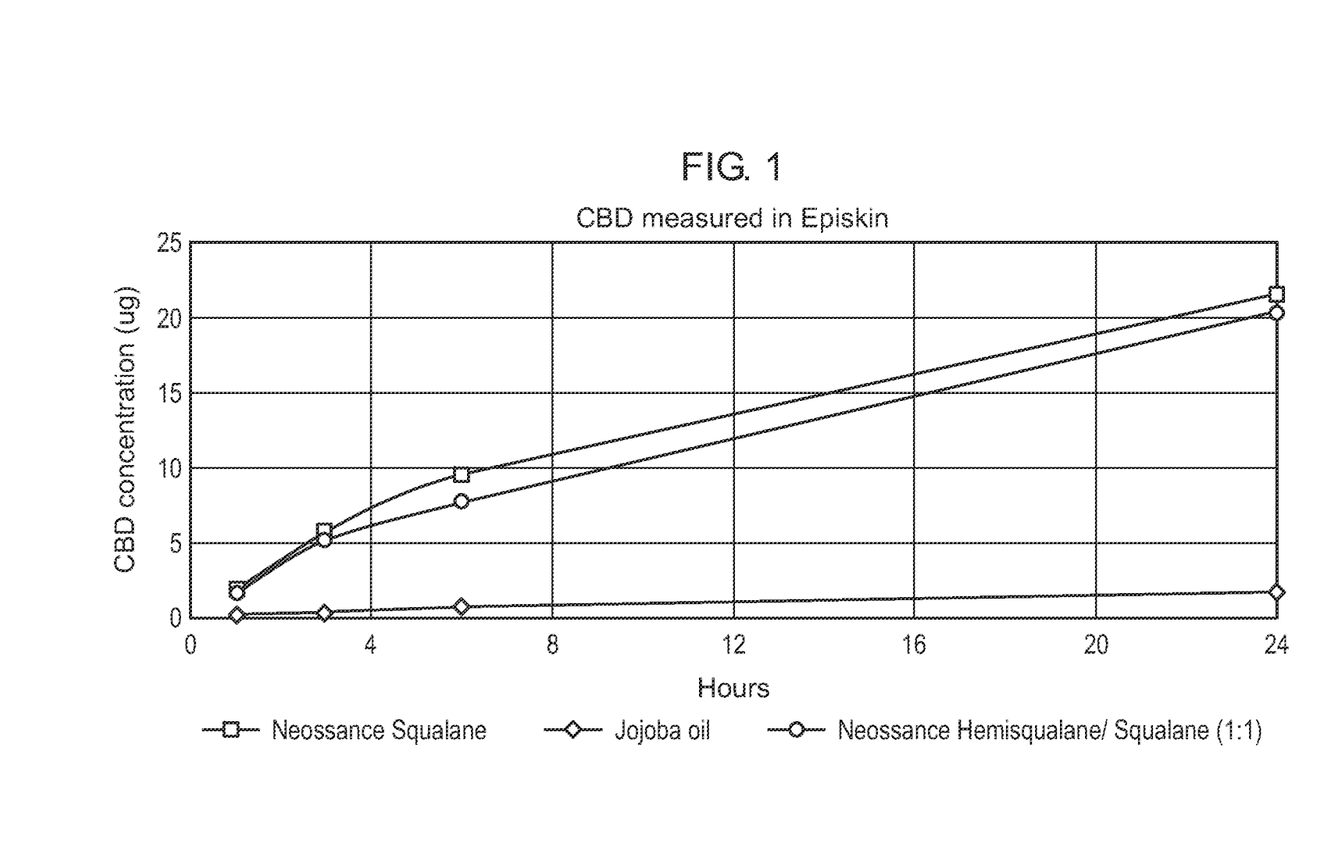
FIG. 1 is a graph showing the comparative delivery of cannabidiol (CBD) in an in vitro human skin model using three different carriers: squalane, squalane/hemisqualane (1:1 w/w mixture), and jojoba oil.

The amount of CBD in the skin cell fraction of the skin cell model is shown in Table 3. As shown in FIG. 1, both squalane and the squalane/hemisqualane mixture facilitated marked penetration and delivery of CBD into the skin cells of the model over the 24-hour period of the experiment. In contrast, jojoba oil did not facilitate the penetration or delivery of CBD over the same time period.

The amount of CBD in the receptor fluid fraction is shown in Table 4. At the 24-hour time point both squalane and the squalane/hemisqualane mixture facilitated the permeation of CBD to the receptor fluid but jojoba oil failed to deliver any CBD to the receptor fluid fraction. The amount of CBD remaining in the wash fraction is shown in Table 5. There was no significant difference between the three carriers in the amount of CBD in the wash fraction.

TABLE 3

CBD amount in the skin model

| Time | Sample | CBD amount (μg) | | | | | |
|---|---|---|---|---|---|---|---|
| | | 1 | 2 | 3 | Mean | ± | SD |
| 1 h | Squalane | 2.10 | 1.83 | 1.68 | 1.87 | ± | 0.21 |
| | Jojoba oil | 0.16 | 0.15 | 0.14 | 0.15 | ± | 0.01 |
| | Hemisqualane/Squalane mixture (1:1) | 1.48 | 1.76 | 1.60 | 1.61 | ± | 0.14 |
| 3 h | Squalane | 5.66 | 5.74 | 5.78 | 5.73 | ± | 0.06 |
| | Jojoba oil | 0.27 | 0.40 | 0.43 | 0.37 | ± | 0.09 |
| | Hemisqualane/Squalane mixture (1:1) | 5.08 | 5.19 | 5.33 | 5.20 | ± | 0.12 |
| 6 h | Squalane | 10.14 | 9.22 | 9.22 | 9.53 | ± | 0.53 |
| | Jojoba oil | 0.72 | 0.65 | 0.71 | 0.70 | ± | 0.04 |
| | Hemisqualane/Squalane mixture (1:1) | 8.60 | 7.29 | 7.18 | 7.69 | ± | 0.79 |
| 24 h | Squalane | 21.41 | 21.39 | 21.94 | 21.58 | ± | 0.31 |
| | Jojoba oil | 1.83 | 1.63 | 1.71 | 1.73 | ± | 0.10 |
| | Hemisqualane/Squalane mixture (1:1) | 21.55 | 19.83 | 19.87 | 20.42 | ± | 0.98 |

TABLE 4

CBD amount in the receptor fluid

| Time | Sample | CBD concentration (μg) | | | | | |
|---|---|---|---|---|---|---|---|
| | | 1 | 2 | 3 | Mean | ± | SD |
| 1 h | Squalane | 0.00 | 0.00 | 0.00 | 0.00 | ± | 0.00 |
| | Jojoba oil | 0.00 | 0.00 | 0.00 | 0.00 | ± | 0.00 |
| | Hemisqualane/Squalane mixture (1:1) | 0.00 | 0.00 | 0.00 | 0.00 | ± | 0.00 |
| 3 h | Squalane | 0.00 | 0.00 | 0.00 | 0.00 | ± | 0.00 |
| | Jojoba oil | 0.00 | 0.00 | 0.00 | 0.00 | ± | 0.00 |
| | Hemisqualane/Squalane mixture (1:1) | 0.00 | 0.00 | 0.00 | 0.00 | ± | 0.00 |
| 6 h | Squalane | 0.00 | 0.00 | 0.00 | 0.00 | ± | 0.00 |
| | Jojoba oil | 0.00 | 0.00 | 0.00 | 0.00 | ± | 0.00 |
| | Hemisqualane/Squalane mixture (1:1) | 0.00 | 0.00 | 0.00 | 0.00 | ± | 0.00 |
| 24 h | Squalane | 0.77 | 1.27 | 1.31 | 1.12 | ± | 0.30 |
| | Jojoba oil | 0.00 | 0.00 | 0.00 | 0.00 | ± | 0.00 |
| | Hemisqualane/Squalane mixture (1:1) | 0.81 | 0.85 | 1.12 | 0.93 | ± | 0.17 |

TABLE 5

CBD amount in the washing

| | | CBD concentration (mg) | | | | | |
|---|---|---|---|---|---|---|---|
| Time | Sample | 1 | 2 | 3 | Mean | ± | SD |
| 1 h | Squalane | 1.33 | 1.38 | 1.31 | 1.34 | ± | 0.03 |
| | Jojoba oil | 1.30 | 1.39 | 1.47 | 1.38 | ± | 0.09 |
| | Hemisqualane/Squalane mixture (1:1) | 1.34 | 1.35 | 1.33 | 1.34 | ± | 0.01 |
| 3 h | Squalane | 1.35 | 1.41 | 1.32 | 1.36 | ± | 0.04 |
| | Jojoba oil | 1.28 | 1.24 | 1.23 | 1.25 | ± | 0.03 |
| | Hemisqualane/Squalane mixture (1:1) | 1.33 | 1.36 | 1.34 | 1.35 | ± | 0.02 |
| 6 h | Squalane | 1.33 | 1.38 | 1.31 | 1.34 | ± | 0.03 |
| | Jojoba oil | 1.30 | 1.39 | 1.47 | 1.38 | ± | 0.09 |
| | Hemisqualane/Squalane mixture (1:1) | 1.34 | 1.35 | 1.33 | 1.34 | ± | 0.01 |
| 24 h | Squalane | 1.38 | 1.38 | 1.36 | 1.37 | ± | 0.01 |
| | Hemisqualane/ | 1.49 | 1.49 | 1.47 | 1.48 | ± | 0.01 |
| | Squalane mixture (1:1) | 1.35 | 1.36 | 1.32 | 1.34 | ± | 0.02 |

The ability of squalane to deliver CBD to skin was compared to the ability of four different carrier oils: sunflower oil, hemp seed oil, caprylic/capric triglyceride, and jojoba oil. Formulations containing 1% CBD in each of the carriers was prepared and applied to the EpiSkin model as described above. The composition of the test samples is shown in Table 6.

TABLE 6

The CBD concentration in test sample

| | CBD concentration (wt %) | | | | | |
|---|---|---|---|---|---|---|
| Sample | 1 | 2 | 3 | Mean | ± | SD |
| 1% CBD/Neossance Squalane | 1.11 | 1.11 | 1.11 | 1.11 | ± | 0.00 |
| 1% CBD/Sunflower Oil | 1.10 | 1.11 | 1.11 | 1.10 | ± | 0.00 |
| 1% CBD/Hemp Seed Oil | 1.12 | 1.12 | 1.12 | 1.12 | ± | 0.00 |
| 1% CBD/Caprylic/Capric Triglyceride | 1.10 | 1.10 | 1.11 | 1.11 | ± | 0.00 |

Figure 2:
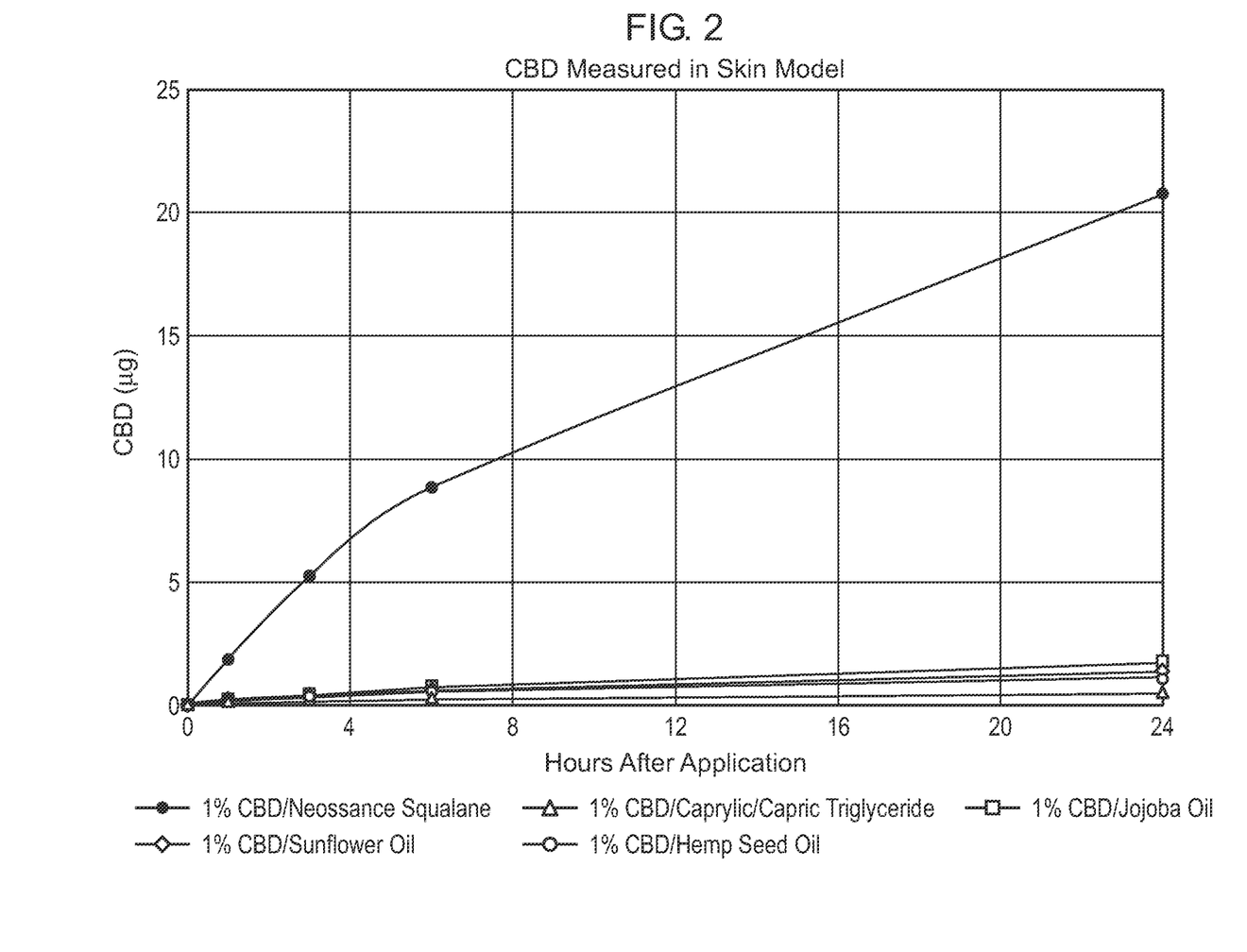
FIG. 2 is a graph showing the comparative delivery of cannabidiol (CBD) in an in vitro human skin model using five different carriers: squalane, sunflower oil, hemp seek oil, caprylic/capric triglyceride, and jojoba oil.

The amount of CBD in the skin cell fraction of the skin cell model is shown in Table 7, the amount of CBD in the receptor fluid is shown in Table 8, and the amount of CBD in the washing is shown Table 9. The results of CBD delivery over time for each carrier are shown in FIG. 2, which demonstrates that squalane is able to deliver over 20 micrograms of CBD after 24 hours. In contrast, sunflower oil, hemp seed oil, caprylic/capric triglyceride, and jojoba oil failed delivered less than 3 micrograms of CBD over the same time period. These results demonstrate that squalane has heightened ability to deliver cannabinoid to skin compared to other known carrier oils.

TABLE 7

CBD amount in the skin model

| | | CBD amount (μg) | | | | | |
|---|---|---|---|---|---|---|---|
| Time | Sample | 1 | 2 | 3 | Mean | ± | SD |
| 1 h | 1% CBD/Neossance Squalane | 1.77 | 2.10 | 1.68 | 1.85 | ± | 0.22 |
| | 1% CBD/Sunflower Oil | 0.20 | 0.29 | 0.15 | 0.21 | ± | 0.07 |
| | 1% CBD/Hemp Seed Oil | 0.13 | 0.15 | 0.11 | 0.13 | ± | 0.02 |

TABLE 7-continued

CBD amount in the skin model

| | | CBD amount (μg) | | | | | |
|---|---|---|---|---|---|---|---|
| Time | Sample | 1 | 2 | 3 | Mean | ± | SD |
| | 1% CBD/Caprylic/Capric Triglyceride | 0.08 | 0.07 | 0.05 | 0.07 | ± | 0.02 |
| 3h | 1% CBD/Neossance Squalane | 4.89 | 5.54 | 3.73 | 4.72 | ± | 0.92 |
| | 1% CBD/Sunflower Oil | 0.38 | 0.36 | 0.32 | 0.36 | ± | 0.03 |
| | 1% CBD/Hemp Seed Oil | 0.30 | 0.35 | 0.28 | 0.31 | ± | 0.03 |
| | 1% CBD/Caprylic/Capric Triglyceride | 0.10 | 0.15 | 0.11 | 0.12 | ± | 0.02 |
| 6 h | 1% CBD/Neossance Squalane | 8.17 | 8.07 | 8.24 | 8.16 | ± | 0.08 |
| | 1% CBD/Sunflower Oil | 0.58 | 0.53 | 0.59 | 0.57 | ± | 0.03 |
| | 1% CBD/Hemp Seed Oil | 0.51 | 0.56 | 0.53 | 0.53 | ± | 0.02 |
| | 1% CBD/Caprylic/Capric Triglyceride | 0.23 | 0.19 | 0.23 | 0.22 | ± | 0.02 |
| 24 h | 1% CBD/Neossance Squalane | 20.84 | 19.47 | 19.54 | 19.95 | ± | 0.77 |
| | 1% CBD/Sunflower Oil | 1.23 | 1.37 | 1.43 | 1.34 | ± | 0.10 |
| | 1% CBD/Hemp Seed Oil | 1.16 | 1.01 | 1.15 | 1.11 | ± | 0.09 |
| | 1% CBD/Caprylic/Capric Triglyceride | 0.50 | 0.38 | 0.47 | 0.45 | ± | 0.06 |

TABLE 8

CBD amount in the receptor fluid

| | | CBD amount (μg) | | | | | |
|---|---|---|---|---|---|---|---|
| Time | Sample | 1 | 2 | 3 | Mean | ± | SD |
| 1 h | 1% CBD/Neossance Squalane | 0.00 | 0.00 | 0.00 | 0.00 | ± | 0.00 |
| | 1% CBD/Sunflower Oil | 0.00 | 0.00 | 0.00 | 0.00 | ± | 0.00 |
| | 1% CBD/Hemp Seed Oil | 0.00 | 0.00 | 0.00 | 0.00 | ± | 0.00 |
| | 1% CBD/Caprylic/Capric Triglyceride | 0.00 | 0.00 | 0.00 | 0.00 | ± | 0.00 |
| 3 h | 1% CBD/Neossance Squalane | 0.00 | 0.00 | 0.00 | 0.00 | ± | 0.00 |
| | 1% CBD/Sunflower Oil | 0.00 | 0.00 | 0.00 | 0.00 | ± | 0.00 |
| | 1% CBD/Hemp Seed Oil | 0.00 | 0.00 | 0.00 | 0.00 | ± | 0.00 |
| | 1% CBD/Caprylic/Capric Triglyceride | 0.00 | 0.00 | 0.00 | 0.00 | ± | 0.00 |
| 6 h | 1% CBD/Neossance Squalane | 0.00 | 0.00 | 0.00 | 0.00 | ± | 0.00 |
| | 1% CBD/Sunflower Oil | 0.00 | 0.00 | 0.00 | 0.00 | ± | 0.00 |
| | 1% CBD/Hemp Seed Oil | 0.00 | 0.00 | 0.00 | 0.00 | ± | 0.00 |
| | 1% CBD/Caprylic/Capric Triglyceride | 0.00 | 0.00 | 0.00 | 0.00 | ± | 0.00 |
| 24 h | 1% CBD/Neossance Squalane | 0.94 | 0.89 | 0.87 | 0.90 | ± | 0.03 |
| | 1% CBD/Sunflower Oil | 0.00 | 0.00 | 0.00 | 0.00 | ± | 0.00 |
| | 1% CBD/Hemp Seed Oil | 0.00 | 0.00 | 0.00 | 0.00 | ± | 0.00 |
| | 1% CBD/Caprylic/Capric Triglyceride | 0.00 | 0.00 | 0.00 | 0.00 | ± | 0.00 |

TABLE 9

CBD amount in the washing

| | | CBD amount (μg) | | | | | |
|---|---|---|---|---|---|---|---|
| Time | Sample | 1 | 2 | 3 | Mean | ± | SD |
| 1 h | 1% CBD/Neossance Squalane | 1.07 | 1.39 | 1.27 | 1.24 | ± | 0.16 |
| | 1% CBD/Sunflower Oil | 1.22 | 1.19 | 1.25 | 1.22 | ± | 0.03 |
| | 1% CBD/Hemp Seed Oil | 1.31 | 1.27 | 1.31 | 1.30 | ± | 0.02 |
| | 1% CBD/Caprylic/Capric Triglyceride | 1.35 | 1.37 | 1.35 | 1.36 | ± | 0.01 |

TABLE 9-continued

CBD amount in the washing

| | | CBD amount (μg) | | | | | |
|---|---|---|---|---|---|---|---|
| Time | Sample | 1 | 2 | 3 | Mean | | SD |
| 3 h | 1% CBD/Neossance Squalane | 1.18 | 1.28 | 1.29 | 1.25 | ± | 0.06 |
| | 1% CBD/Sunflower Oil | 1.46 | 1.41 | 1.42 | 1.43 | ± | 0.03 |
| | 1% CBD/Hemp Seed Oil | 1.51 | 1.48 | 1.47 | 1.49 | ± | 0.02 |
| | 1% CBD/Caprylic/Capric Triglyceride | 1.50 | 1.48 | 1.25 | 1.41 | ± | 0.14 |
| 6 h | 1% CBD/Neossance Squalane | 1.26 | 1.31 | 1.30 | 1.29 | ± | 0.03 |
| | 1% CBD/Sunflower Oil | 1.43 | 1.43 | 1.45 | 1.44 | ± | 0.01 |
| | 1% CBD/Hemp Seed Oil | 1.55 | 1.54 | 1.54 | 1.54 | ± | 0.01 |
| | 1% CBD/Caprylic/Capric Triglyceride | 1.53 | 1.56 | 1.52 | 1.54 | ± | 0.02 |
| 24 h | 1% CBD/Neossance Squalane | 1.26 | 1.34 | 1.40 | 1.33 | ± | 0.07 |
| | 1% CBD/Sunflower Oil | 1.48 | 1.46 | 1.48 | 1.48 | ± | 0.01 |
| | 1% CBD/Hemp Seed Oil | 1.56 | 1.61 | 1.61 | 1.59 | ± | 0.03 |
| | 1% CBD/Caprylic/Capric Triglyceride | 1.57 | 1.53 | 1.60 | 1.56 | ± | 0.04 |

What is claimed:

1. A method of delivering a cannabinoid to a subject comprising applying a composition comprising a carrier and one or more cannabinoids to a skin area of the subject, wherein the carrier comprises squalane.

2. The method of claim 1, wherein the composition is applied to the skin area in an amount of from about 0.1 mg/cm$^2$ to about 10 mg/cm$^2$.

3. The method of claim 2, wherein the composition is applied to the skin area in an amount of from about 1 mg/cm$^2$ to about 3 mg/cm$^2$.

4. The method of claim 1, wherein an effective amount of cannabinoid is delivered to the subject.

5. The method of claim 1, wherein an effective amount of the composition is administered to the skin of the subject to reduce inflammation.

6. The method of claim 5, wherein the composition is administered at least daily.

7. The method of claim 6, wherein the composition is administered at least twice daily.

8. The method of claim 1, an effective amount of the composition is administered the skin of the subject to reduce pain.

9. The method of claim 1, wherein the one or more cannabinoids comprise cannabigerol (CBG) or cannabidiol (CBD).

10. A method of reducing inflammation in skin of a subject comprising applying an effective amount of a composition comprising a carrier and one or more cannabinoids to a skin area of the subject, thereby reducing inflammation, wherein the carrier comprises squalane.

11. The method of claim 10, wherein the composition is administered to the skin area in an amount of from about 0.1 mg/cm$^2$ to about 10 mg/cm$^2$.

12. The method of claim 11, wherein the composition is administered to the skin area in an amount of from about 1 mg/cm$^2$ to about 3 mg/cm$^2$.

13. The method of 10, wherein the composition is administered at least daily.

14. The method of claim 13, wherein the composition is administered at least twice daily.

15. The method of claim 10, wherein the one or more cannabinoids comprise cannabigerol (CBG) or cannabidiol (CBD).

16. A method of reducing pain in a subject comprising applying an effective amount of a composition comprising a carrier and one or more cannabinoids to a skin area of the subject, thereby reducing pain, wherein the carrier comprises squalane.

17. The method of claim 16, wherein the composition is administered to the skin area in an amount of from about 0.1 mg/cm$^2$ to about 10 mg/cm$^2$.

18. The method of claim 17, wherein the composition is administered to the skin area in an amount of from about 1 mg/cm$^2$ to about 3 mg/cm$^2$.

19. The method of 16, wherein the composition is administered at least daily.

20. The method of claim 16, wherein the one or more cannabinoids comprise cannabigerol (CBG) or cannabidiol (CBD).

* * * * *